United States Patent
Grubb et al.

(10) Patent No.: US 9,169,289 B2
(45) Date of Patent: Oct. 27, 2015

(54) PEPTIDE DERIVATIVES FOR TREATMENT, PREVENTION OR ALLEVIATION OF A CONDITION ASSOCIATED WITH BONE LOSS OR LOW BONE DENSITY OR TO INHIBIT OSTEOCLAST DIFFERENTIATION AND STIMULATION

(71) Applicant: Strongbone AB, Gothenburg (SE)

(72) Inventors: Anders Grubb, Lund (SE); Franciszek Kasprzykowski, Gdandski (PL); Ulf Lerner, Umea (SE); Beata Zolnowska, Gdansk (PL); Regina Kasprzykowska, Gdandski (PL)

(73) Assignee: STRONGBONE AB, Gothenburg (SE)

( * ) Notice: Subject to any disclaimer, the term of this patent is extended or adjusted under 35 U.S.C. 154(b) by 0 days.

(21) Appl. No.: 14/257,255

(22) Filed: Apr. 21, 2014

(65) Prior Publication Data

US 2014/0243274 A1    Aug. 28, 2014

Related U.S. Application Data

(62) Division of application No. 13/379,146, filed as application No. PCT/SE2010/050682 on Jun. 17, 2010, now Pat. No. 8,748,370.

(60) Provisional application No. 61/220,006, filed on Jun. 24, 2009.

(30) Foreign Application Priority Data

Jun. 18, 2009 (SE) ...................... 0900834

(51) Int. Cl.
| | |
|---|---|
| A61K 38/00 | (2006.01) |
| A61P 19/08 | (2006.01) |
| A61P 19/02 | (2006.01) |
| A61P 19/10 | (2006.01) |
| C07K 7/06 | (2006.01) |
| C07K 5/062 | (2006.01) |
| C07K 5/072 | (2006.01) |
| C07K 5/107 | (2006.01) |
| C07K 5/11 | (2006.01) |
| C07D 207/16 | (2006.01) |
| C07K 5/06 | (2006.01) |
| C07K 5/08 | (2006.01) |
| C07K 5/10 | (2006.01) |

(52) U.S. Cl.
CPC ............... *C07K 7/06* (2013.01); *C07D 207/16* (2013.01); *C07K 5/06* (2013.01); *C07K 5/06043* (2013.01); *C07K 5/06052* (2013.01); *C07K 5/06095* (2013.01); *C07K 5/08* (2013.01); *C07K 5/10* (2013.01); *C07K 5/1016* (2013.01); *C07K 5/1019* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,858,581 B2 | 2/2005 | Kuhner et al. | |
| 8,097,582 B2 | 1/2012 | Grubb et al. | |
| 8,748,370 B2 * | 6/2014 | Grubb et al. | 514/1.1 |
| 2002/0103161 A1 | 8/2002 | Weigele et al. | |

FOREIGN PATENT DOCUMENTS

| | | |
|---|---|---|
| EP | 0504938 A2 | 9/1992 |
| WO | 9917709 A2 | 4/1999 |
| WO | 0194332 A1 | 12/2001 |
| WO | 2006052201 A1 | 5/2006 |
| WO | 2007129952 A1 | 11/2007 |

OTHER PUBLICATIONS

Dattani, Femoral osteolysis following total hip replacement (Postgrad Med J 2007;83:312-316).*
Drugwatch.com (retrieved online on Sep. 29, 2014 from URL: < http://www.drugwatch.com/hip-replacement/complications/>).*
Nair et al, Clinical Isolates of Staphylococcus Aureus Have Osteolytic Surface Proteins and a Proportion of the Population Have Antibodies That Block This Activity] Is This of Prognostic Significance? (British Journal of Rheumatology, 1997;36:328-332).*
Abouassaly et al, Antibiotic-coated medical devices: with an emphasis on inflatable penile prosthesis (Asian J Androl Sep. 2004; 6: 249-257).*
Buchholtz, Late infections after artificial joint replacement with a septic course (Chirurg. Sep. 1979;50(9):573-5).*
Nair et al, Surface-Associated Proteins from Staphylococcus aureus Demonstrate Potent Bone Resorbing Activity (Journal of Bone and Mineral Research, vol. 10, No. 5, 1995).*
Bossard et al., "Proteolytic Activity of Human Osteoclast Cathepsin K", The Journal of Biological Chemistry, 1996, vol. 271, No. 21, pp. 12517-12524, XP002918429.
Franski et al., "Formation of stoichiometric complexes between dibenzo-30-crown-10 and guanidinium moiety containing compounds", International Journal of Mass Spectrometry, 2007, vol. 266, pp. 180-184, XP022231889.
Kasprzykowski et al., "The Antibacterial Peptides Structurally Based on N-terminal Binding Part of Cystatin C", pp. 790-791, XP008152772.
Ramjee et al., "Substrate mapping and inhibitor profiling of falcipain-2, falcipain-3 and berghepain-2: implications for peptidase anti-malarial drug discovery", Biochemical Journal, 2006, vol. 399, pp. 47-57, XP009115415.

(Continued)

*Primary Examiner* — Karlheinz R Skowronek
*Assistant Examiner* — Sergio Coffa
(74) *Attorney, Agent, or Firm* — Young & Thompson

(57) ABSTRACT

Compounds of formula $R^1$-A-NH—CH($R^2$)—CO—$R^3$ are presented. The compounds can be used to treat or alleviate conditions associated with bone loss or low bone density, or to inhibit osteoclast differentiation and stimulation, bone resorption and/or loosening of a prosthetic device. The compounds can be administered as a pharmaceutical composition or in a prosthetic device.

9 Claims, 1 Drawing Sheet

(56) References Cited

OTHER PUBLICATIONS

Ranganathan D et al., "Transformation of C-terminal and threonine extended precursors into C-terminal alpha-amidated peptides: A possible chemical model for the alpha amidating action of pituitary enzymes", J Am Chem Soc, 113, pp. 1042-1044.

Shigezane K, "Synthesis of antirenin active peptides", Yakugaku Zasshi, 91 (9), pp. 987-996, 1971.

Rival et al. "Dipeptide derivative synthesis catalyzed by Pseudomonas aeruginosa elastase", J Peptide Research, 53, 1999, pp. 170-176.

Wieczerzak E, "An enormously active and selective azapeptide inhibitor of cathepsin B", Journal of Peptide Science 13(8), 536-543, (2007).

Juszczyk P. et al. "Simple and efficient synthesis of chiral amino alcohols with an amino acid-based skeleton", Letters in Peptide Science, 10, pp. 79-82, (2003).

Kasprzykowski F et al. Synthesis and antibacterial properties of peptidyl derivatives and cyclopeptides structurally based upon the inhibitory centre of human cystatin C., APMIS 108, pp. 473-481 (2000).

Mattingly Phillip G. "Mono-Protected Diamines. Nα-tert-Butoxycarbonyl x, w-Alkanediamine Hydrochlorides from Amino alcohols." Papers, Synthesis, Apr. 1990, pp. 366-368.

Dougherty, "Pathobiology of Infection in Prosthetic Devices", Reviews of Infectious Diseases, vol. 10, No. 6 (Nov.-Dec. 1988), pp. 1102-1117.

International Search Report, dated Sep. 22, 2010, in PCT/SE2010/050682.

* cited by examiner

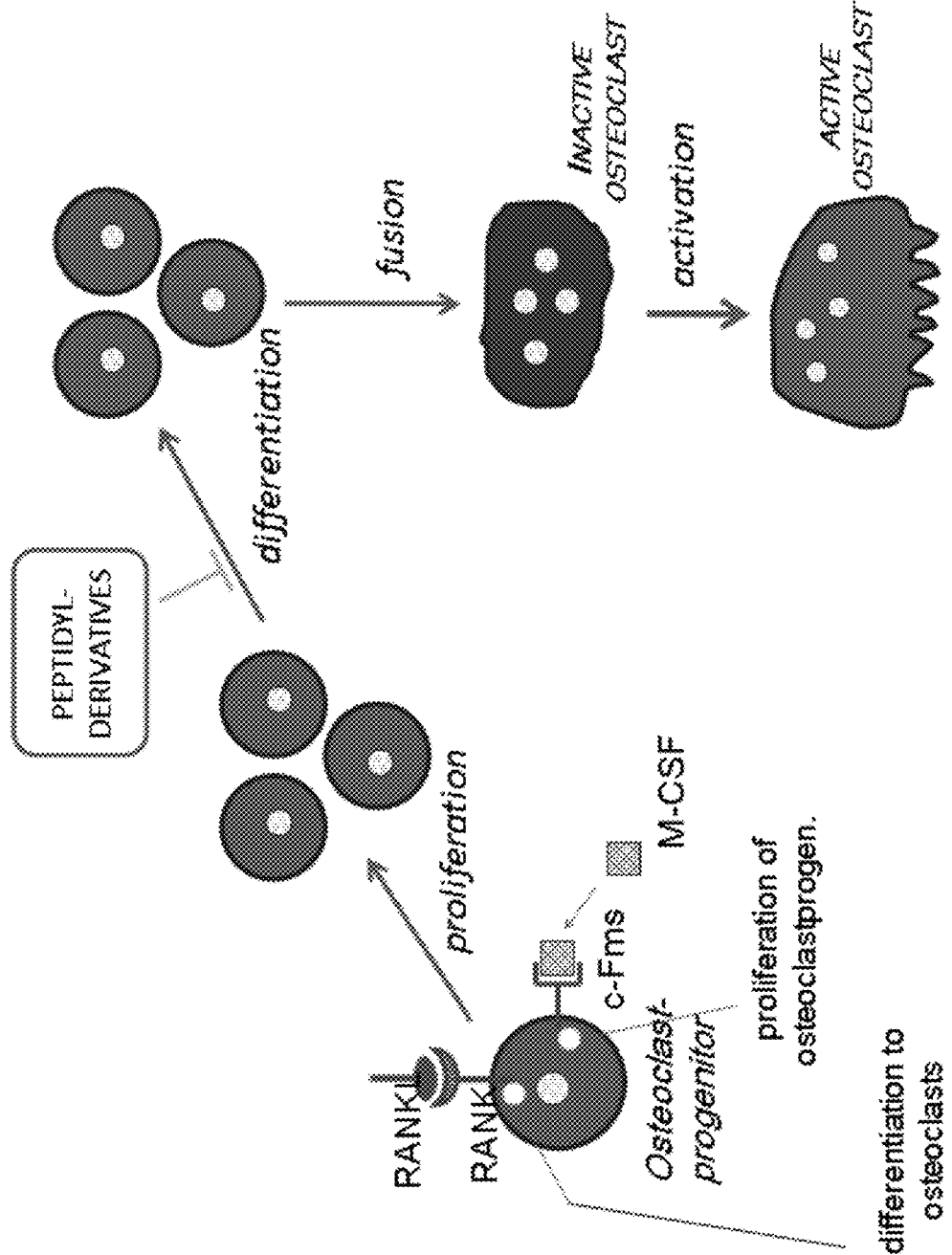

PEPTIDE DERIVATIVES FOR TREATMENT, PREVENTION OR ALLEVIATION OF A CONDITION ASSOCIATED WITH BONE LOSS OR LOW BONE DENSITY OR TO INHIBIT OSTEOCLAST DIFFERENTIATION AND STIMULATION

FIELD OF INVENTION

The invention relates to novel compounds which may be for treatment, prevention or alleviation of a condition associated with bone loss or low bone density or to inhibit osteoclast differentiation and stimulation, bone resorption, or loosening of a prosthetic device.

BACKGROUND OF INVENTION

There is an increasing demand for the development of compounds having improved properties and which can be used against several different diseases, such as treatment of an infection or disease caused by a microorganism as well as for the stimulation or inhibition of the proliferation of eukaryotic cells as well as for other purposes.

One class of compounds, namely peptide derivatives based upon the inhibitory centre of human cystatin C, and the antibacterial properties thereof have been disclosed in Kasprzykowski et al., APMIS 2000, 108, 473-481.

WO 06/052201 discloses the use of peptide derivatives for the manufacture of a medicament for the treatment of microbial infections.

WO 07/129952 discloses novel peptide derivatives and the use thereof as antimicrobial agent for treatment of wounds.

Hitherto no suggestions have been given for use of the mentioned peptide derivatives other than for antimicrobial and antibacterial purposes.

Osteoclasts constitute one type of eukaryotic cells. Bone resorption is a specific function of osteoclasts, which are multinucleated, specialized bone cells formed by the fusion of mononuclear progenitors originating from the haemopoietic compartment, more precisely from the granulocyte-macrophage colony-forming unit (GM-CFU). The osteoclast is the principal cell type for resorption of bone. Osteoclasts together with the bone-forming cells, the osteoblasts, dictate bone mass, bone shape and bone structure. Bone must undergo continuous resorption and renewal, a process collectively known as remodelling. During adult life bone remodelling is crucial to eliminate and replace structurally damaged or aged bone with structurally new healthy bone. To maintain the proper bone mass, resorption and formation are kept in perfect equilibrium. The balanced bone remodelling is disturbed in certain pathological conditions either to systemic excess or decrease of endocrine factors or the presence of local pathological conditions in the skeleton. In such diseases, the equilibrium between bone resorption and formation becomes altered, often in favour of resorption, resulting in a reduction in bone mass, deterioration of bone architecture, decreased resistance to stress, bone fragility, susceptibility to fractures or to disabilities in joints or teeth. Hence, increased activity and/or numbers of osteoclasts, relative to the activity and/or numbers of osteoblasts, may lead to a pathological loss of bone.

For conditions in which osteoclasts resorb bone at abnormally high levels as in osteoporosis, rheumatoid arthritis, periodontal disease, metastatic tumours, loss of joint prosthesis or tooth implant loss, the most reasonable therapeutic target would be the osteoclast. Decreasing the number of osteoclasts and/or the resorption activity of the osteoclasts, should restore the equilibrium between bone resorption and formation.

SUMMARY OF THE INVENTION

The object of the present invention is a number of invented compounds which prevents osteoclast formation and/or inhibits proteases, such as cystein proteases, which may be used for the manufacture of a medicament for treatment, prevention or alleviation of a condition associated with bone loss or low bone density or to inhibit osteoclast differentiation and stimulation, bone resorption, or loosening of a prosthetic device.

The invention relates in one aspect to a compound of the general formula (I)

wherein
$R^1$ is Ar—X—, where X is $(CH_2)_m$—O—CO; $(CH_2)_m$—$SO_2$—CH=CH—CO; CH=CH—CO; CO—CH=CH—CO; CO-oxirane-CO; or
$R^1$ is Hal-$(CH_2)_m$—CO, where Hal is F, Cl, Br or I; or
$R^1$ is $CH_3$—O—CO-oxirane-CO; or
$R^1$ is $NH_2$—C(NH)—NH—$(CH_2)_m$—CO; or
$R^1$ is an acyl residue containing coumarin moiety, optionally hydroxylated;
A is a bond or is one or more amino acid such as Arg, Val or Leu;
$R^2$ is isopropyl, sec-butyl or isobutyl;
$R^3$ is Pro or Arg-B, where B is NH—NH—CO-Ile-Val-O—$CH_3$; or
$R^3$ is NH—$(CH_2)_m$—NH—C(NH)—$NH_2$; or
$R^3$ is NH—CH($R^4$)—$(CH_2)_m$—NH-D, where $R^4$ is $C_1$-$C_6$-alkyl, such as isopropyl, and D is CO—CH=CH—Ar or CO—CH=CH—$SO_2$—$(CH_2)_m$—Ar, or Cum-Phe-sequence, where Cum is an acyl residue containing coumarin moiety, optionally hydroxylated;
Ar is aryl or heteroaryl, such as phenyl or pyridyl;
m is an integer of 0 to 5;
or
wherein
$R^1$ is Ar—X—, where X is $(CH_2)_m$—O—CO; $(CH_2)_m$—$SO_2$—CH=CH—CO; CH=CH—CO; CO-oxirane-CO; CO—CH=CH—CO; $CH_2$—CH=CH—CO; $(CH_2)_m$—CO or
$R^1$ is $CH_3$—O—CO-oxirane-CO; or
$R^1$ is $NH_2$—C(NH)—NH—$(CH_2)_m$—CO; or
$R^1$ is an acyl residue containing coumarin moiety, optionally hydroxylated;
A is a bond or is one or more amino acid such as Arg, Val or Leu;
$R^2$ is isopropyl or isobutyl;
$R^3$ is NH—$(CH_2)_m$—NH—C(NH)—$NH_2$; or
$R^3$ is Phe-$NH_2$; or
$R^3$ is NH—CH($R^4$)—$(CH_2)_m$—NH-D, where $R^4$ is $C_1$-$C_6$-alkyl, such as isopropyl, and D is CO—CH=CH—Ar or CO—CH=CH—$SO_2$—$(CH_2)_m$—Ar, or Cum-Phe-sequence, where Cum is an acyl residue containing coumarin moiety, optionally hydroxylated;
Ar is aryl or heteroaryl, such as phenyl or pyridyl;
m is an integer of 0 to 5;
as a single stereoisomer or a mixture of different stereoisomers;
or a pharmaceutically acceptable salt thereof.

By the new invented compounds it is for the first time possible to treat, prevent or alleviate conditions associated with bone loss or low bone density or to inhibit osteoclast differentiation and stimulation, bone resorption, or loosening of a prosthetic device.

Further advantages and objects with the present invention will be described in more detail, inter alia with reference to the accompanying drawings.

BRIEF DESCRIPTION OF THE DRAWINGS

FIG. 1 shows osteoclast formation.

DETAILED DESCRIPTION OF THE INVENTION

Definitions

In the context of the present application and invention, the following definitions apply:

The term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions and aqueous dextrose and glycerol solutions are preferably employed as carriers, particularly for injectable solutions. Suitable pharmaceutical carriers are described in "Remington's Pharmaceutical Sciences" by E. W. Martin.

In the present application an arrow "←" found when defining a sequence indicates the direction of the amide bond of the subsequent group.

In the present application the expression "Valψ(CH$_2$NH)" means that the peptide (amide) bond is reduced.

The Compound

The invention relates to the unexpected finding that the compounds of the invention having the general formula (I)

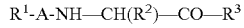

R$^1$-A-NH—CH(R$^2$)—CO—R$^3$ wherein
R$^1$ is Ar—X—, where X is (CH$_2$)$_m$—O—CO; (CH$_2$)$_m$—SO$_2$—CH=CH—CO; CH=CH—CO; CO—CH=CH—CO; CO-oxirane-CO; or
R$^1$ is Hal-(CH$_2$)$_m$—CO, where Hal is F, Cl, Br or I; or
R$^1$ is CH$_3$—O—CO-oxirane-CO; or
R$^1$ is NH$_2$—C(NH)—NH—(CH$_2$)$_m$—CO; or
R$^1$ is an acyl residue containing coumarin moiety, optionally hydroxylated;
A is a bond or is one or more amino acid such as Arg, Val or Leu;
R$^2$ is isopropyl, sec-butyl or isobutyl;
R$^3$ is Pro or Arg-B, where B is NH—NH—CO-Ile-Val-O—CH$_3$; or
R$^3$ is NH—(CH$_2$)$_m$—NH—C(NH)—NH$_2$; or
R$^3$ is NH—CH(R$^4$)—(CH$_2$)$_m$—NH-D, where R$^4$ is C$_1$-C$_6$-alkyl, such as isopropyl, and D is CO—CH=CH—Ar, CO—CH=CH—SO$_2$—(CH$_2$)$_m$—Ar, or Cum-Phe-sequence, where
Cum is an acyl residue containing coumarin moiety, optionally hydroxylated;

Ar is aryl or heteroaryl, such as phenyl or pyridyl;
m is an integer of 0 to 5;
or
wherein
R$^1$ is Ar—X—, where X is (CH$_2$)$_m$—O—CO; (CH$_2$)$_m$—SO$_2$—CH=CH—CO; CH=CH—CO; CO-oxirane-CO; CO—CH=CH—CO, CH$_2$—CH=CH—CO; (CH$_2$)$_m$—CO or
R$^1$ is CH$_3$—O—CO-oxirane-CO; or
R$^1$ is NH$_2$—C(NH)—NH—(CH$_2$)$_m$—CO; or
R$^1$ is an acyl residue containing coumarin moiety, optionally hydroxylated;
A is a bond or is one or more amino acid such as Arg, Val or Leu;
R$^2$ is isopropyl or isobutyl;
R$^3$ is NH—(CH$_2$)$_m$—NH—C(NH)—NH$_2$; or
R$^3$ is Phe-NH$_2$; or
R$^3$ is NH—CH(R$^4$)—(CH$_2$)$_m$—NH-D, where R$^4$ is C$_1$-C$_6$-alkyl, such as isopropyl, and D is CO—CH=CH—Ar, CO—CH=CH—SO$_2$—(CH$_2$)$_m$—Ar, or Cum-Phe-sequence, where Cum is an acyl residue containing coumarin moiety, optionally hydroxylated;
Ar is aryl or heteroaryl, such as phenyl or pyridyl;
m is an integer of 0 to 5;
as a single stereoisomer or a mixture of different stereoisomers;
or a pharmaceutically acceptable salt thereof, results in inhibition of osteoclast differentiation, formation, or function, leads to less bone resorption, As such, these compounds may be used to treat a subject having a condition characterized by bone loss. These compounds may be especially well suited for treatment, prevention or alleviation of a condition associated with systemic bone loss or low bone density or to inhibit osteoclast differentiation and stimulation, bone resorption, or loosening of a prosthetic device, such as a bone disease associated with primary or secondary osteoporosis, juvenile osteoporosis, osteogenesis imperfecta, hypercalcaemia, hyperparathyroidism, osteomalacia, osteohalisteresis, osteolytic bone disease, osteonecrosis and Paget's disease of bone or a condition being a secondary osteoporosis such as bone loss due to rheumatoid arthritis, inflammatory arthritis, osteomyelitis, bone loss due to an eating disorder, metastatic bone diseases, periodontal bone loss, bone loss due to cancer and age-related loss of bone or bone resorption induced by pharmaceuticals or implantates. Examples of implantates include prosthetic joint implantation as well as dental and other implantations. Other conditions where facilitation of bone repair or replacement is desired such as bone fractures, bone defects, plastic surgery. It was determined that the invented compounds inhibit osteoclast formation. These results suggest that the invented compounds may be useful in the treatment of all the diseases/disorder or conditions mentioned above.

FIG. 1 describes that steoclasts are giant cells with several nuclei and they are the only cells in nature which can resorb bone (breakdown of bone) and they do so by adhering to bone tissue and creating a resorption lacunae. The bone tissue is resorb in the lacuane by a two step process in which the osteoclasts dissolve mineral crystals by creating an acid pH in the resorption lacunae and degrade the bone protein matrix by releasing proteolytic enzymes, including cysteine proteinases like cathepsin K. These giant cells are formed from mononuclear precursor cells from bone marrow. It is required that such precursor cells are stimulated by the cytokines M-CSF (macrophage colony-stimulating factor) and RANKL (receptor activator of nuclear factor kappa B ligand). M-CSF is needed for the precursor cells to proliferate and RANKL for that they can differentiate (become specialized) to cells which eventually fuse to the inactive osteoclasts which then can adhere to bone and become active. The compounds of the invention do not affect the proliferative step but inhibits the differentiation pathway.

In specific embodiments $R^1$ is Ar—$(CH_2)_m$—O—CO or $NH_2$—CH(NH)—NH—$(CH_2)_m$—CO and/or $R^2$ is isobutyl and/or $R^3$ is NH—$(CH_2)_m$—NH—CH(NH)—$NH_2$. In one specific embodiment $R^1$ is (7-hydroxycoumarin-4-yl)acetyl residue.

The compound according to the present invention may be selected from any of the following:

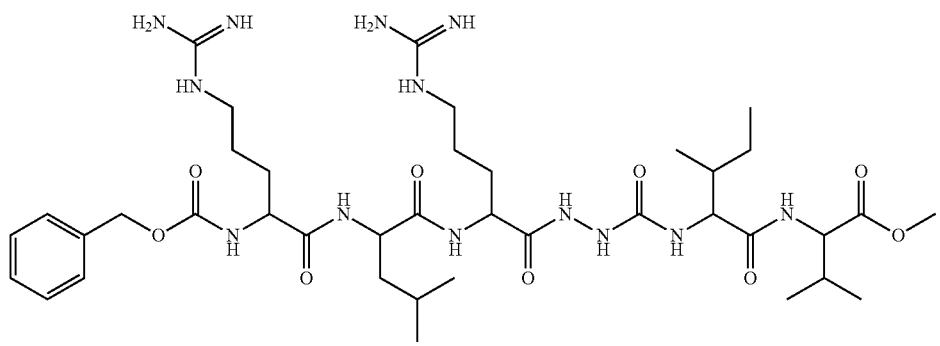

Z-RLR
Sequence: Z-Arg-Leu-Arg-Agly-Ile-Val-OMe

M-1

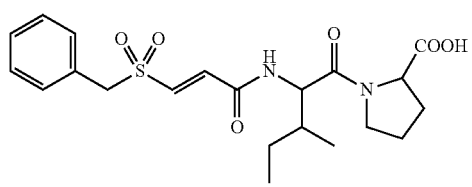

Sequence: Bzsa-Ile-Pro-OH
FW = 436.2

A11

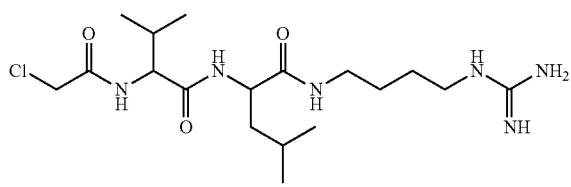

Sequence: ClAc-Val-Leu-Agm
FW = 418.2

A12

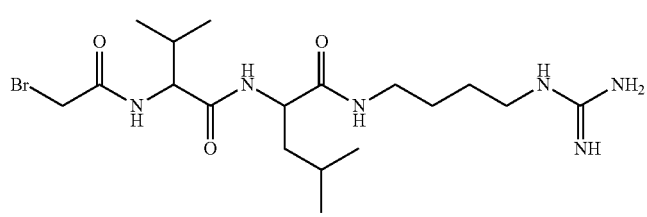

Sequence BrAc-Val-Leu-Agm
FW = 463.4

A-20

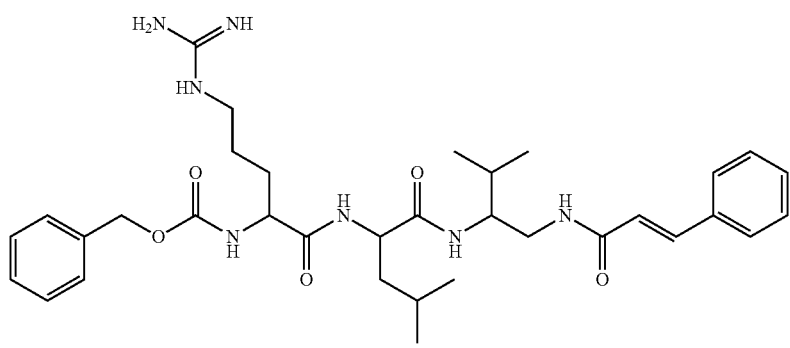

Sequence: Z-Arg-Leu-NH—CH(iPr)—$CH_2$—NH ← Cin

-continued
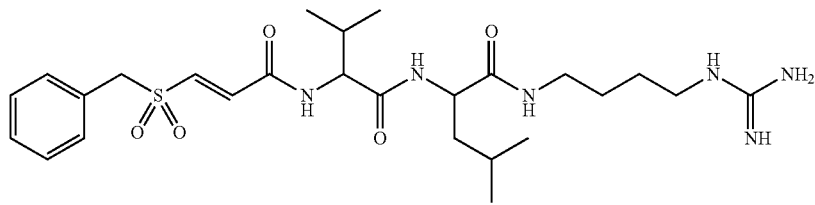
Sequence: Bzsa-Val-Leu-Agm
FW = 550.7
A25
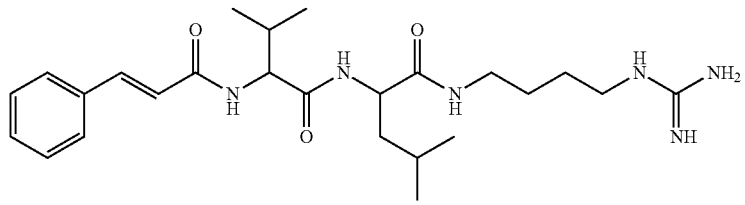
Sequence: Cin-Val-Leu-Agm
FW = 472.6
A-26
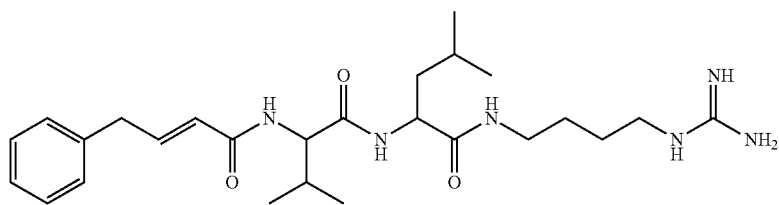
Sequence: Bac-Leu-Val-Agm
Where Bac = 3-benzylacroyl and Agm = agmatine
(decarboxyarginine) residue
A-30
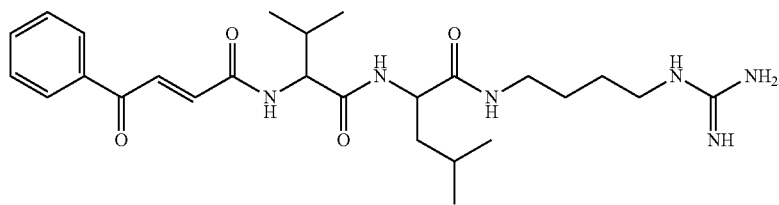
Sequence: Bzac-Val-Leu-Agm
FW = 500.6
A-33
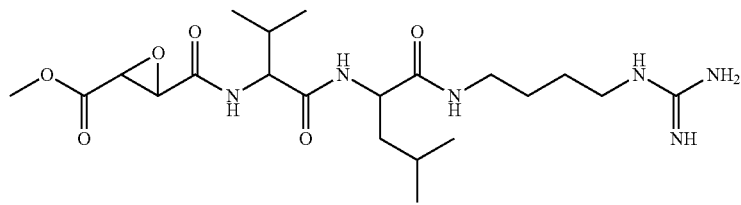
Sequence: MeO-Eps-Val-Leu-Agm
FW = 470.6
A-42

-continued
A-47
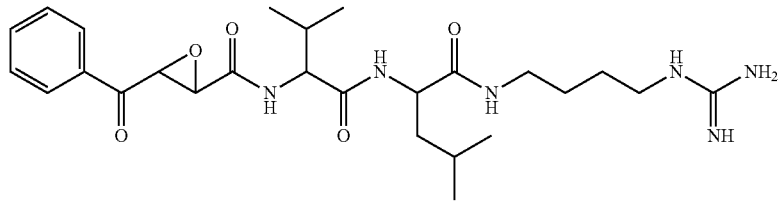
Sequence: (2S,3S)Bga-Val-Leu-Agm
FW = 516.6
A-49
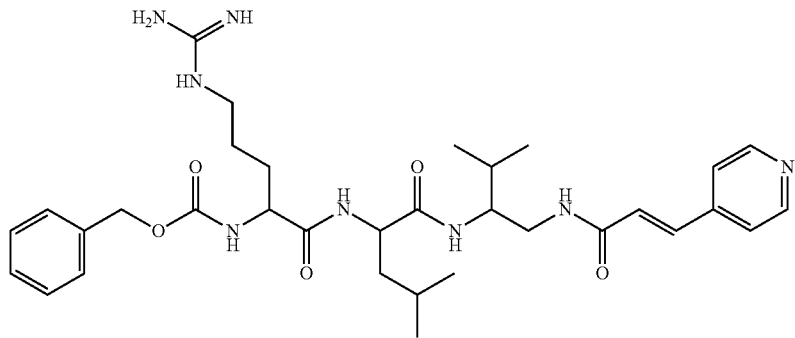
Sequence: Z-Arg-Leu-NH—CH(iPr)—CH₂—NH ← 4-Pac
A-50
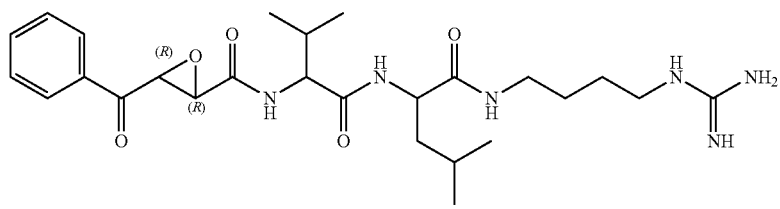
Sequence: (2R,3R)Bga-Val-Leu-Agm
FW = 516.6
A107
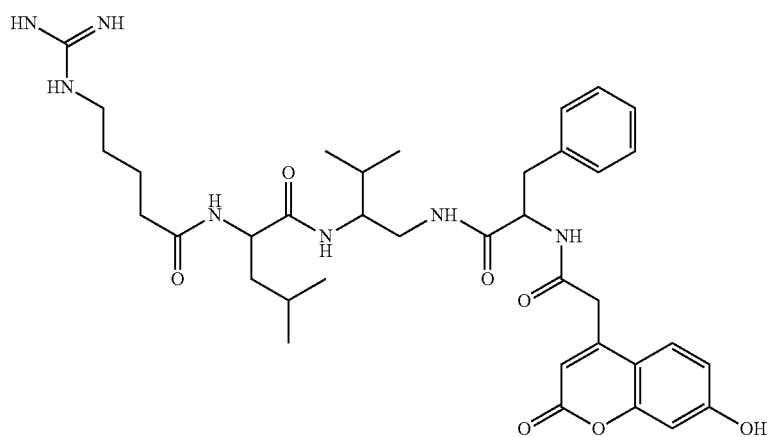

A54
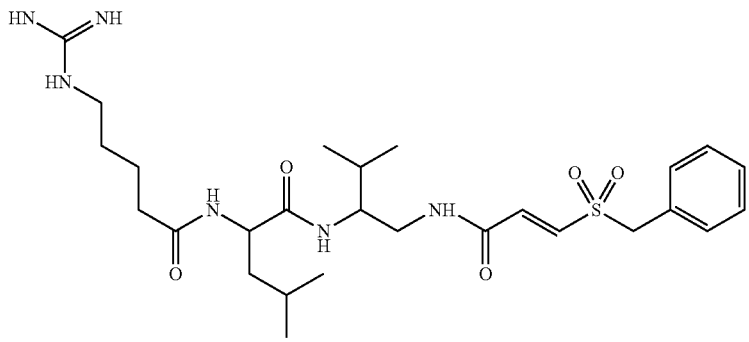
A-59
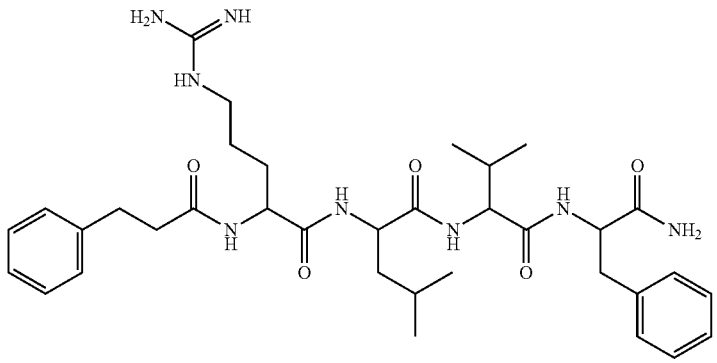
Sequence: Ppa-Arg-Leu-Val-Phe-NH₂ or dPhe-Arg-Leu-Phe-NH₂
where Ppa = dPhe = deamino-Phe = 3-phenylpropionic acid
A-113
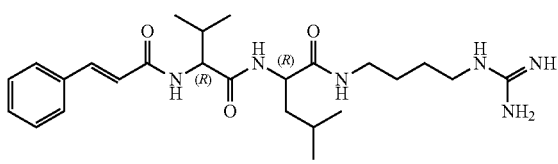
Sequence: Cin-ᴅVal-ᴅLeu-Agm
A-114
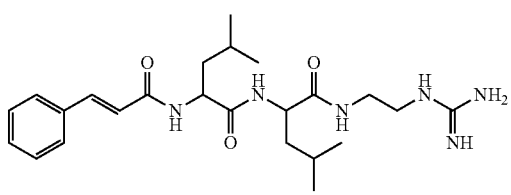
Sequence: Cin-Leu-Leu-NH—(CH₂)₂ NH—(C=NH)—NH₂
A-116
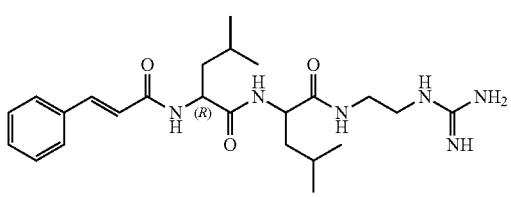
Sequence: Cin-ᴅLeu-Leu-NH—(CH₂)₂—NH—(C=NH)—NH₂
A-118
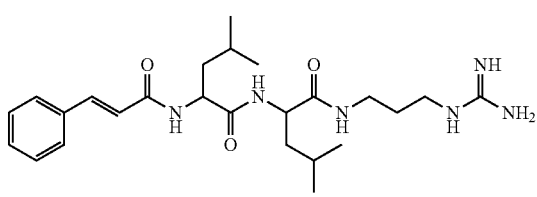
Sequence: Cin-Leu-Leu-NH—(CH₂)₂—NH—(C=NH)—NH₂
A-119
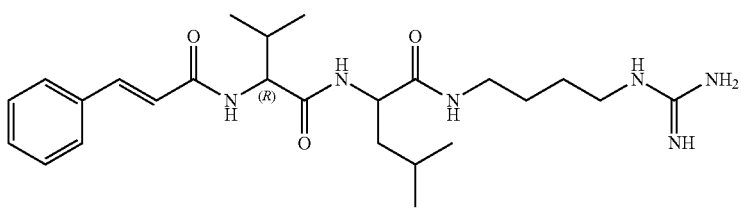
Sequence: Cin-ᴅVal-Leu-Agm

A-120

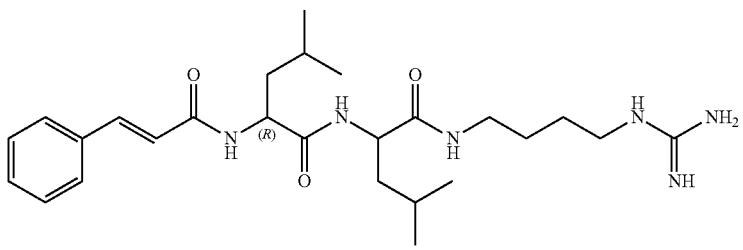

Sequence: Cin-DLeu-Leu-Agm

A-123

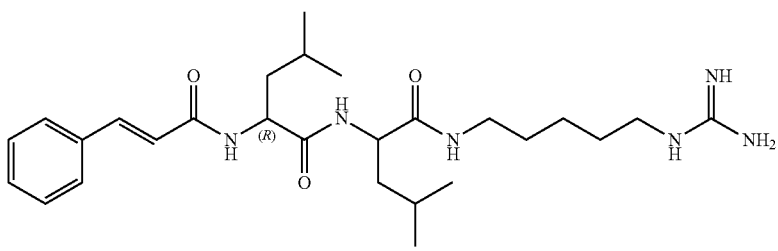

Sequence: Cin-DLeu-Leu-NH—(CH₂)₅—NH—(C═NH)—NH₂

A-127

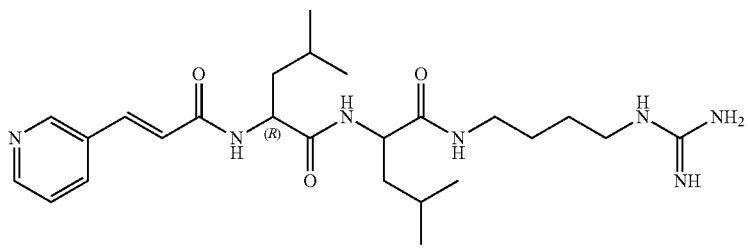

Sequence: 3Pac-DLeu-Leu-Agm

A-128

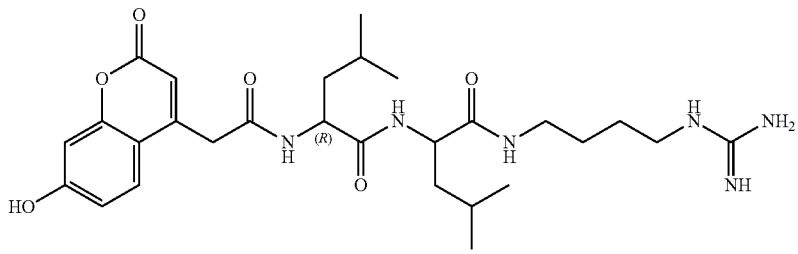

Sequence: Cum-DLeu-LeuNH—(CH₂)₄NH—(C═NH)—NH₂

FW = 558,7 as a single stereoisomer or a mixture of different stereoisomers;
or a pharmaceutically acceptable salt thereof.

In one embodiment the compound is selected from any of the following compounds:

Z-RLR, M-1; A11, A12, A25, A33, A42, A47, A50, A54, A107, A127 and A128 as a single stereoisomer or a mixture of different stereoisomers or a pharmaceutically acceptable salt thereof. Said compounds are as defined above.

In another embodiment the compound is selected from the following:

Z-RLR, M-1, A11, A-47, A-54, A-107, A-127 and A-128 as a single stereoisomer or a mixture of different stereoisomers; or a pharmaceutically acceptable salt thereof.

In a further embodiment the compound is selected from the following compounds:

A-20, A-25, A-26, A-30, A-33, A-47, A-49, A-50, A-54, A-59, A-107, A-116, A-118, A-119, A-120, A-123, A-127 and A-128 as a single stereoisomer or a mixture of different stereoisomers; or a pharmaceutically acceptable salt thereof.

In another embodiment the compound is selected from any of the following compounds:

A-20, A-25, A-26, A-30, A-33, A-47, A-49, A-50, A-54, A-59 as a single stereoisomer or a mixture of different stereoisomers; or a pharmaceutically acceptable salt thereof.

In yet another embodiment the compound is selected from any of the following compounds:

A-59, A-107, A-116, A-118, A-119, A-120, A-123, A-127 and A-128 as a single stereoisomer or a mixture of different stereoisomers; or a pharmaceutically acceptable salt thereof.

In yet another embodiment the compound is the compound denoted A59 as defined above, as a single stereoisomer or a mixture of different stereoisomers; or a pharmaceutically acceptable salt thereof.

The compounds according to the present invention are potential cysteine proteases inhibitors and/or possesses antimicrobial properties, for example compounds denoted A-25 A-33, A-54, A-59 and A-107 and A-20

The invention also relates to the use of any of the above mentioned compounds or a compound selected from any of the following:

A-16

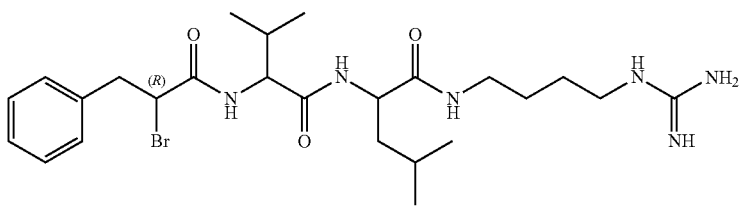

Sequence BrPpr-Val-Leu-Agm
FW = 552.2

A-30

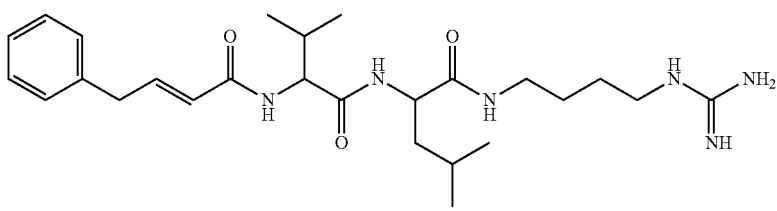

Sequence: Bac-Val-Leu-Agm
FW = 486.7

A-91

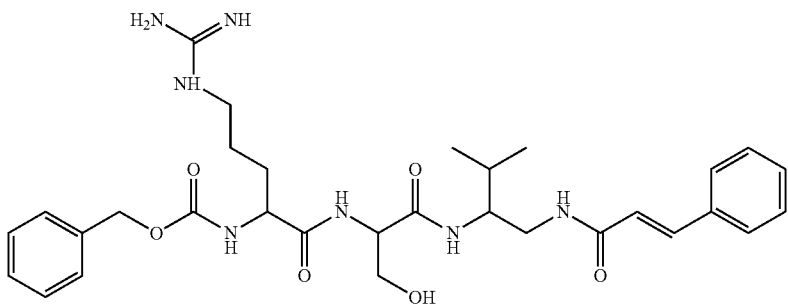

Z-Arg-Ser-Valψ[CH₂NH]-Cin
FW = 623.7

A-96

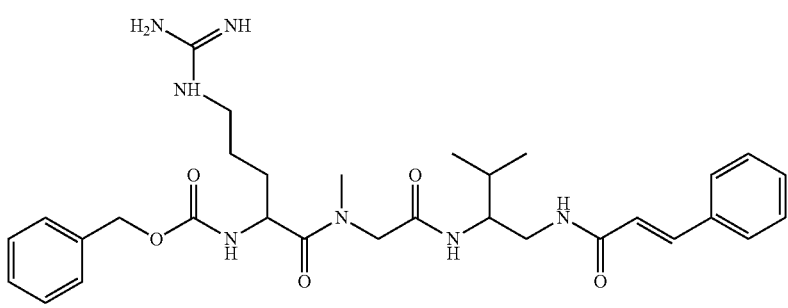

Sequence: Z-Arg-Sar-Valψ[CH₂NH]-Cin
FW = 607.7

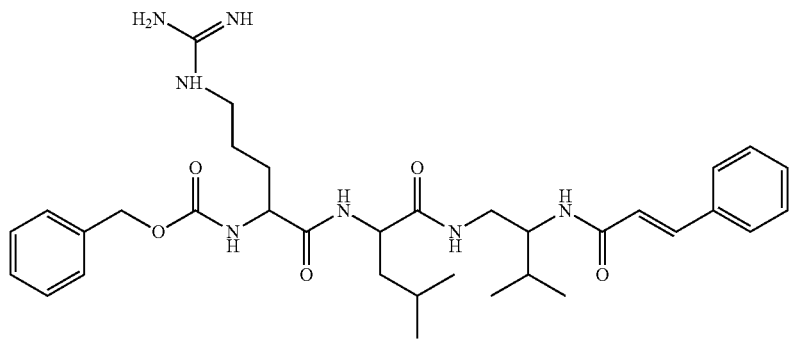
A-97
Sequence: Z-Arg-Leu ← [NHCH₂]ψVal ← Cin
FW = 635.7
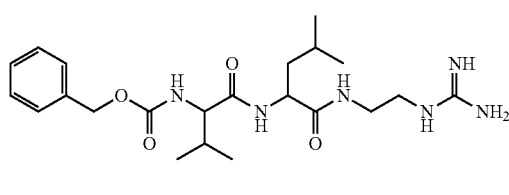
A-98
Sequence: Z-Val-Leu-NH(CH₂)₂—NH(C=NH)—NH₂
FW = 448.6
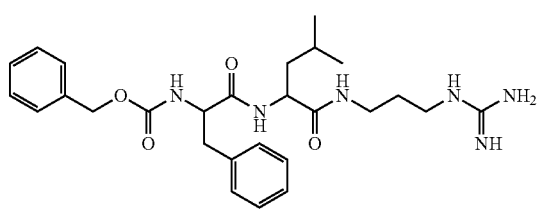
A-99
Sequence: Z-Phe-Leu-NH(CH₂)₃—NH(C=NH)—NH₂
FW = 510.6
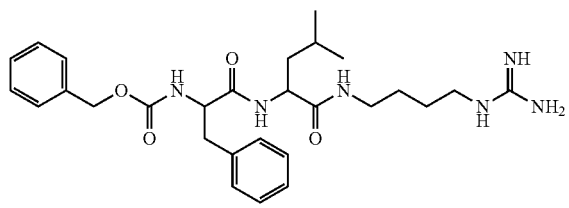
Sequence: Z-Phe-Val-Agm
FW = 524.7
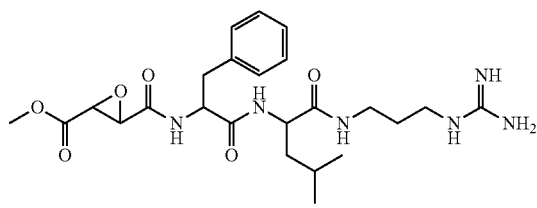
A-100
Sequence: MeO-Eps-Phe-Leu-Agm
FW = 518.6
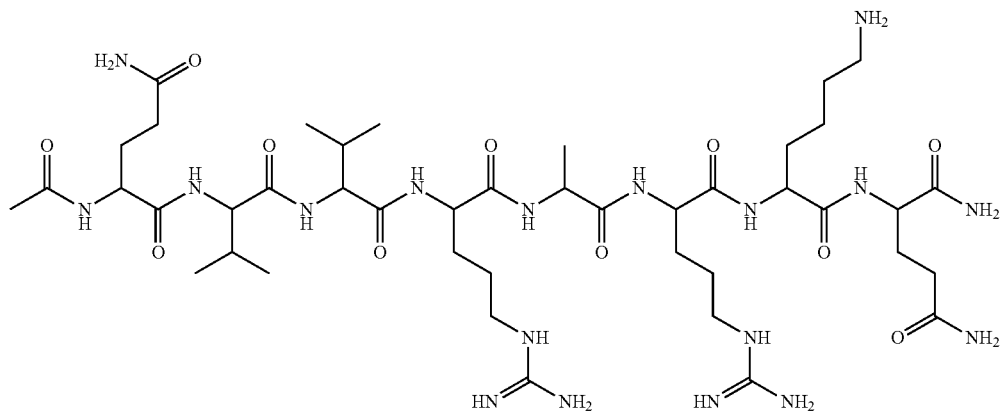
A-102
Sequence: Ac-Gln-Val-Val-Arg-Ala-Arg-Lys-Gln-NH₂
FW = 1025.2

A-103
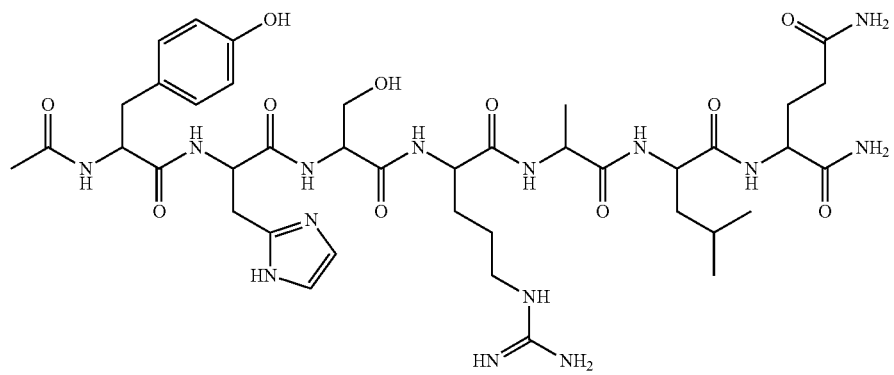
Sequence: Ac-Tyr-His-Ser-Arg-Ala-Leu-Gln-NH₂
FW = 915.0
A-104
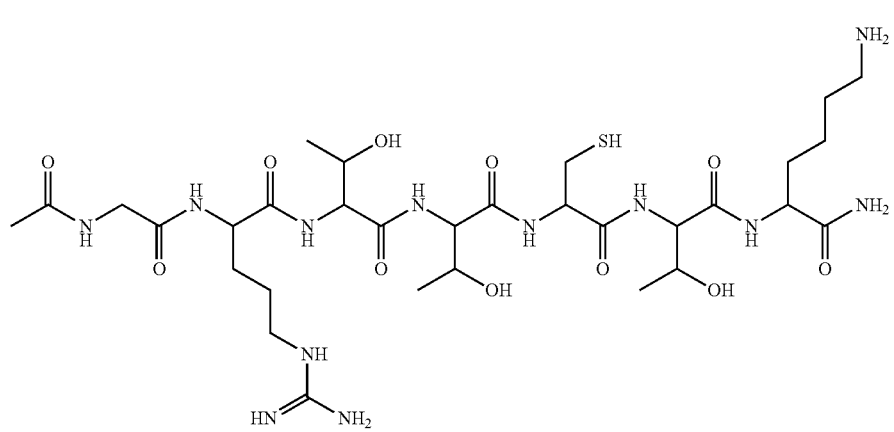
Sequence: Ac-Arg-Thr-Thr-Cys-Thr-Lys-NH₂
FW = 749.9
A-105
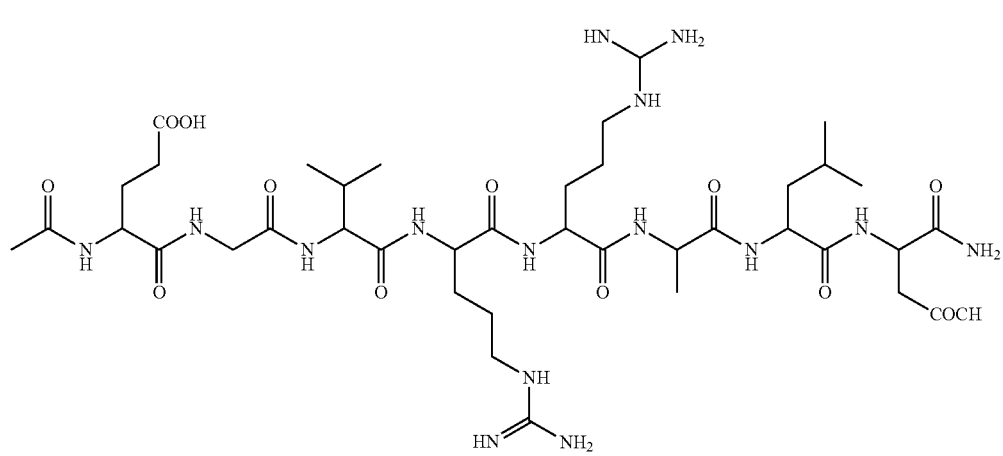
Sequence: Ac-Glu-Gly-Val-Arg-Arg-Ala-Leu-Glu-NH₂
FW = 970.1

A-106
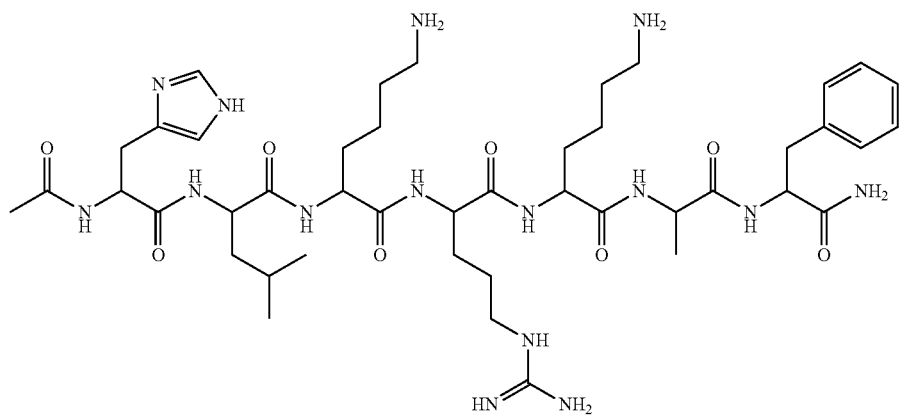
Ac-His-Leu-Lys-Arg-Lys-Ala-Phe-NH₂
FW = 940.1
A-108
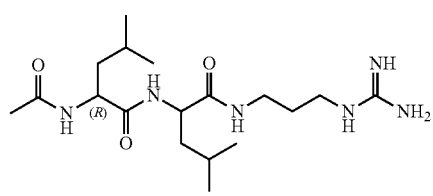
Sequence Ac-DLeu-Val-NH—(CH₂)₃—NH—(C=NH)—NH₂
A-115
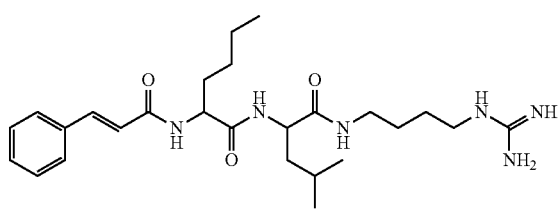
Sequence: Cin-Nle-Leu-Agm
A-117
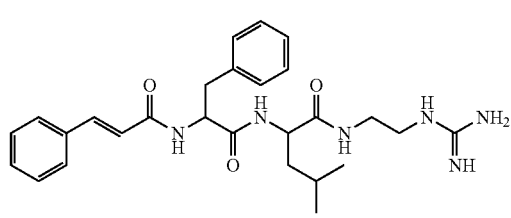
Sequence: Cin-Phe-Leu-NH—(CH₂)₂—NH—(C=NH)—NH₂
A-121
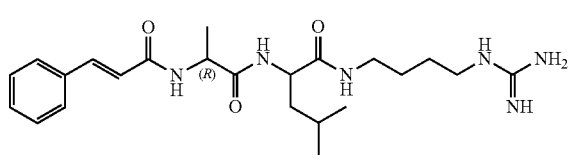
Sequence: Cin-DAla-Leu-Agm
A-122
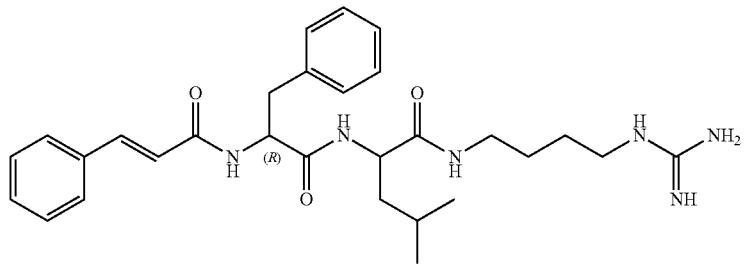
Sequence: Cin-DPhe-Leu-Agm
A-124
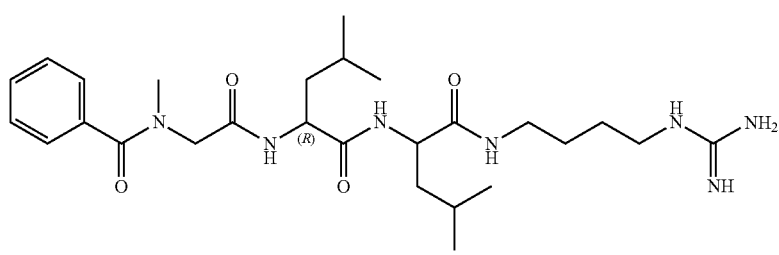
Sequence: Bz-Sar-DLeu-Leu-Agm

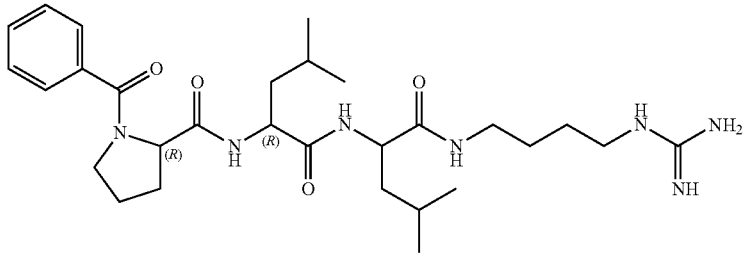

Sequence: Bz-_D_Pro-_D_Leu-Agm

A-125

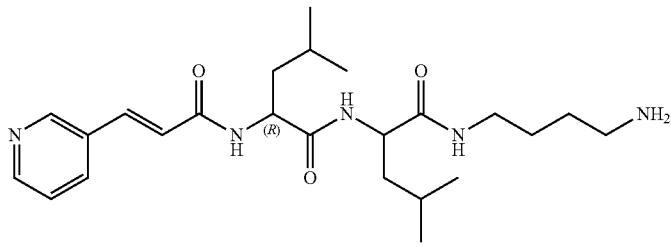

Sequence: 3Pac-_D_Leu-Leu-NH—(CH$_2$)$_4$NH$_2$

A-126 as a single stereoisomer or a mixture of different stereoisomers; or a pharmaceutically acceptable salt thereof, for the manufacture of a medicament for treatment, prevention or alleviation of a condition associated with bone loss or low bone density or to inhibit osteoclast differentiation and stimulation, bone resorption, or loosening of a prosthetic device, wherein the condition is a bone disease selected from osteoporosis, juvenile osteoporosis, osteogenesis imperfecta, hypercalcaemia, hyperparathyroidism, osteomalacia, osteohalisteresis, osteolytic bone disease, osteonecrosis and Paget's disease of bone or a condition being a secondary osteoporosis such as bone loss due to rheumatoid arthritis, inflammatory arthritis, osteomyelitis, bone loss due to an eating disorder, metastatic bone diseases, periodontal bone loss, bone loss due to cancer and age-related loss of bone or bone resorption induced by pharmaceuticals or implantates.

Pharmaceutical Compositions

Candidates for therapy with the compounds/agents identified by the methods described herein are patients either suffering from bone loss, bone resorption or patients who have a medical prosthesis implanted or who contemplate receiving an implant medical prosthetic device. The pharmaceutical formulation may be administrated when a candidate suffer from a disease or disorder as well as be given prophylactic.

The invention provides methods of treatment featuring administering to a subject an effective amount of a compound/agent of the invention. The compound is preferably substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. Accordingly, the compound/agents synthesized by the methods described herein may be formulated as pharmaceutical compositions to be used for prophylaxis or therapeutic use to treat these patients.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilising agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the compound can be delivered in a vesicle, in particular a liposome (Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327)

In yet another embodiment, the compound can be delivered in a controlled or sustained release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321: 574). In another embodiment, polymeric materials can be used (See, Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., (1983) Macromol. Sci. Rev. Macromol. Chem. 23:61; Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the subject bone or prosthesis, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

The present invention further contemplates therapeutic compositions useful in practicing the therapeutic methods of this invention. A subject therapeutic composition includes, in admixture, a pharmaceutically acceptable excipient (carrier) and one or more of the compounds described herein as an active ingredient.

The present compounds or agents that are described herein can be used as the sole active agents, or can be used in combination with one or more other active ingredients. These agents are known in the art, and can be selected from anti-inflammatory compounds, bisphosphonates, soluble RANK, anti-RANKL, OPG and bone morphogenetic proteins, for instance.

When contemplating combination therapy with the compounds defined herein and one or more of the above-noted agents, it is important to assess clinical safety by methods known to those skilled in the art. Appropriate dose titration may be necessary when certain groups of compounds are contemplated for use together.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Preferably, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treating it with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the preferred embodiment, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). A hydrogel is defined as a substance formed when an organic polymer (natural or synthetic) is cross-linked via covalent, ionic, or hydrogen bonds to create a three-dimensional open-lattice structure which entraps water molecules to form a gel. In general, these polymers are at least partially soluble in aqueous solutions, such as water, buffered salt solutions, or aqueous alcohol solutions, which have charged side groups, or a monovalent ionic salt thereof.

For use in treating animal subjects, the compositions of the invention can be formulated as pharmaceutical or veterinary compositions. Depending on the subject to be treated, the mode of administration, and the type of treatment desired, e.g., prevention, prophylaxis, therapy; the compositions are formulated in ways consonant with these parameters. A summary of such techniques is found in Remington's Pharmaceutical Sciences, latest edition, Mack Publishing Co., Easton, Pa.

The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Formulations may be prepared in a manner suitable for systemic administration or for topical or local administration. Systemic formulations include, but are not limited to those designed for injection (e.g., intramuscular, intravenous or subcutaneous injection) or may be prepared for transdermal, transmucosal, nasal, or oral administration. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. The formulation will generally include a diluent as well as, in some cases, adjuvants, buffers, preservatives and the like. In addition, if desired, the composition can contain minor amounts of auxiliary substances such as wetting or emulsifying agents, pH buffering agents which enhance the effectiveness of the active ingredient.

The compounds defined above can be formulated into the therapeutic composition as neutralized pharmaceutically acceptable salt forms. Pharmaceutically acceptable salts include the acid addition salts (formed with the compounds) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. For oral administration, the compositions can be administered also in liposomal compositions or as microemulsions. Suitable forms include syrups, capsules, tablets, as is understood in the art.

The compositions of the present invention may also be administered locally to sites in subjects, both human and other vertebrates, such as domestic animals, rodents and livestock, using a variety of techniques known to those skilled in the art. For example, these may include sprays, lotions, gels or other vehicles such as alcohols, polyglycols, esters, oils and silicones.

The administration of the compositions of the present invention may be pharmacokinetically and pharmacodynamically controlled by calibrating various parameters of administration, including the frequency, dosage, duration mode and route of administration. Variations in the dosage, duration and mode of administration may also be manipulated to produce the activity required.

The therapeutic compound compositions defined herein are conventionally administered in the form of a unit dose, for instance intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the agent selected for treating the subject, the dosage formulation, and in a therapeutically effective amount. The desired effect refers to the effect of the agent on reducing or inhibiting osteoclast differentiation and activity by reducing or inhibiting bone resorption. Moreover, the quantity of the compound to be administered depends on the subject to be treated as well as the extent or severity of bone resorption. Precise amounts of active ingredient required to be administered depend on the judgment of the practitioner and are peculiar to each individual. However, suitable dosages to achieve the desired therapeutic effect in vivo may range from about 0.1 mg/kg body weight per day to about 200 mg/kg body weight per day, or from about 1.0 mg/kg body weight per day to about 100 mg/kg body weight per day, preferably about 25 mg/kg body weight per day to about 50 mg/kg body weight per day. The preferred dose will depend on the route of administration. However, dosage levels are highly dependent on the nature of the disease or situation, the condition of the subject, the judgment of the practitioner, and the frequency and mode of administration. If the oral route is employed, the absorption of the substance will be a factor effecting bioavailability. A low absorption will have the effect that in the gastrointestinal tract higher concentrations, and thus higher dosages, will be necessary. Suitable regimes for initial administration and further administration are also variable, but are typified by an initial administration followed by repeated doses at one or more hour intervals by a subsequent injection or other administration. Alternatively, continuous intravenous infusion sufficient to maintain desired concentrations, e.g. in the blood, are contemplated. The composition may be administered as a single dose multiple doses or over an established period of time in an infusion.

It will be understood that the appropriate dosage of the substance should suitably be assessed by performing animal model tests, where the effective dose level (e.g., $ED_{50}$) and the toxic dose level (e.g. $TD_{50}$) as well as the lethal dose level (e.g. $LD_{50}$ or $LD_{10}$) are established in suitable and acceptable animal models. Further, if a substance has proven efficient in such animal tests, controlled clinical trials should be performed.

The compounds or compositions of the present invention may be modified or formulated for administration at the site of pathology. Such modification may include, for instance, formulation which facilitate or prolong the half-life of the compound or composition, particularly in the environment. Additionally, such modification may include the formulation of a compound or composition to include a targeting protein or sequence which facilitates or enhances the uptake of the compound/composition to bone or bone precursor cells. In a particular embodiment, such modification results in the preferential targeting of the compound to bone or bone precursor cells versus other locations or cells. In one embodiment, a tetracycline, tetracycline family or bisphosphonate may be utilized to target the compound or composition of the present invention to bone or bone cells, including osteoclasts and osteoclast precursors. Novel heterocycles as bone targeting compounds are disclosed in U.S. Patent Publication No. 2002/0103161 A1, which is incorporated herein by reference in its entirety.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Sterile injectable forms of the compositions may be aqueous or oleaginous suspensions. The suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavouring or colouring agents may also be added.

Alternatively, the pharmaceutical compositions may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention includes, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilising or dispersing agents.

The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The invention also provides prosthetic devices having one or more of the compounds defined herein thereon or therein. The compound or compounds may be present in a composition applied to one or more surfaces of the prosthetic device or be present within the prosthetic device. That is, the compound or compounds, may be present within the very matrix of the prosthetic device such as for instance within the cement, e.g. methylmethacrylate cement that forms the prosthetic device.

Following examples are intended to illustrate, but not to limit, the invention in any manner, shape, or form, either explicitly or implicitly.

EXAMPLES

The following abbreviations are used in the examples: THF, tetrahydrofuran; HOBt, hydroxybenzotriazole; DCC, dicyclohexylcarbodiimide; DCU, dicyclohexylurea; TFA, trifluoroacetic acid; DMF, dimethylformamide; DIPEA, N,N-diisopropylethylamine; TBTU,O-(benzotriazol-1yl)-NNN'N'-tetramethyluronium tetrafluoroborate; DCM, dichlormethane, MeOH, methanol; DMSO, dimethylsulfoxide Example 1

Synthesis of Coumarinacetyl-Containing Derivative A-128

4-(tert-butyloxycarbonylamino)butylamine hydrochloride

The 4-(tert-butyloxycarbonylamino)butylamine hydrochloride was obtained from 4-aminobutan-1-ol in accordance with procedures described in literature (Mattingly, P. G., Synthesis, 1990, 1990, 366-368). m.p. 156-158° C.

4-(benzyloxycarbonyl-L-leucylamino)-N-(tert-butoxycarbonyl)butylamine

To a vigorously stirred solution of 4-(tert-butyloxycarbonylamino)-butylamine hydrochloride (0.140 g, 0.624 mmol), Z-L-leucine (0.165 g, 0.624 mmol), HOBt (0.084 g, 0.624 mmol), triethylamine (174 µl, 1.25 mmol) in THF (25 ml) cooled on ice bath, DCC (0.141 g, 0.686 mmol) was added in small portions, during 0.5 h. The mixture was stirred on ice bath for additional 1 h, next left at room temperature overnight. The precipitated DCU was filtered off, washed with THF (2×5 ml) and the combined filtrates were evaporated under reduced pressure. The solid residue was dissolved in ethyl acetate (250 ml) and the solution was washed with 1M hydrochloric acid (3×80 ml), water (100 ml), 1 M sodium bicarbonate (3×80 ml) and brine (2×80 ml). The organic layer was dried over anhydrous magnesium sulphate and evaporated to dryness. The residue was dissolved in ethyl acetate and precipitated with petroleum ether. Yield: 0.220 g (81%) of 4-(benzyloxycarbonyl-L-leucylamino)-N-(tert-butoxycarbonyl)butylamine.

$[\alpha]^{20}_D$=−13.5° (c=1; MeOH), MS MALDI TOF: m/z 458.2 [M+Na]$^+$, 474.1 [M+K]$^+$, calculated for $C_{23}H_{37}N_3O_5$: 435.6.

4-(benzyloxycarbonyl-D-leucyl-L-leucylamino)-N-(tert-butoxycarbonyl)-butylamine 4-(benzyloxycarbonyl-L-leucylamino)-N-(tert-butoxycarbonyl)butylamine (0.210 g, 0,482 mmol) was dissolved in MeOH (25 ml). This solution was hydrogenated over 10% Pd—C catalyst under atmospheric pressure during 1 h at room temperature. Next, the catalyst was filtered off, washed with MeOH (10 ml) and the combined filtrates were evaporated. The resulted 4-(L-leucylamino)-N-(tert-butoxycarbonyl)butylamine (0.199 g, 0.482 mmol) was dissolved in 25 ml of THF and triethylamine (133 µl, 0.964 mmol), next HOBt (0.065 g, 0.482 mmol) and Z-D-leucine (0.128 g, 0.482 mmol) were added to the solution. The stirred mixture was cooled on ice bath and DCC (0.109 g, 0.530 mmol) was added in small portions during 0.5 h. The mixture was stirred in an ice bath for an additional 1 h, then left at room temperature overnight. The precipitated DCU was filtered off, washed with THF (2×5 ml) and the combined filtrates were evaporated under reduced pressure. The solid residue was dissolved in ethyl acetate (200 ml) and the solution was washed with 1M hydrochloric acid (3×70 ml), water (100 ml), 1 M sodium bicarbonate (3×70 ml) and brine (2×70 ml). The organic layer was dried over anhydrous magnesium sulphate and evaporated to dryness. The residue was dissolved in ethyl acetate and precipitated with petroleum ether; yield: 0.219 g (83%) of 4-(benzyloxycarbonyl-D-leucyl-L-leucylamino)-N-(tert-butoxycarbonyl)butylamine.

$[\alpha]^{20}_D$=−1.0° (c=1; MeOH). MS MALDI TOF: m/z 571.4 [M+Na]$^+$, 587.4 [M+K]$^+$, calculated for $C_{29}H_{45}N_4O_6$: 548.7.

N-amidino-4-(benzyloxycarbonyl-D-leucyl-L-leucylamino)butylamine 4-(benzyloxycarbonyl-D-leucyl-L-leucylamino)-N-(tert-butoxycarbonyl)-butylamine (0.209 g, 0.381 mmol) was dissolved in 8 ml of 4N solution of anhydrous hydrochloride in dioxane. The reaction mixture was stirred during 0.5 h at room temperature, then evaporated to dryness under reduced pressure. The residual oil was triturated with anhydrous diethyl ether (25 ml). The obtained solid was filtered off under reduced pressure, washed with anhydrous diethyl ether (3×10 ml) and dried under vacuum over potassium hydroxide. The resulted 4-(benzyloxycarbonyl-D-leucyl-L-leucylamino)butylamine hydrochloride (0.181 g, 0.374 mmol) was dissolved in 8 ml of DMF. Next, triethylamine (104 µl, 0.748 mmol) and 3,5-dimethyl-1-pyrazolylformamidinium nitrate (0.225 g. 1.12 mmol) were added. The pH of the mixture was kept about 9.5. After five days the solution was evaporated and the resulted residue was dissolved in 6 ml of 35% acetonitrile/water solution containing 0.1% TFA (v/v/v). Half of the solution was injected on the RP-HPLC column (25×250 mm, Kromasil C-8, 5 µm) and eluted with 35% acetonitrile/water solution, containing 0.1% TFA (v/v/v) at flow rate 14 ml/mm. (isocratic elution). The eluate was monitored using UV detector at λ=226 nm. Fractions containing pure N-(amidino)-4-(benzyloxycarbonyl-L-leucyl-L-leucylamino)butylamine were collected, concentrated under reduced pressure and lyophilized. The second half of the crude N-(amidino)-4-(benzyloxycarbonyl-L-leucyl-L-leucylamino)butylamine solution was purified in the same manner.

Yield: 0.110 g (60%) of product as trifluoroacetate salt.
MS MALDI TOF: m/z 491.4 [M+H]$^+$, 513.4 [M+Na]$^+$, 529.4 [M+K]$^+$, calculated for $C_{25}H_{42}N_6O_4$: 490.6.

N-amidino-4-(7-hydroxy-4-coumarinacetyl-D-leucyl-L-leucylamino)butylamine

N-Amidino-4-(benzyloxycarbonyl-D-leucyl-L-leucylamino)butylamine (0.100 g, 0.2O4 mmol) was dissolved in MeOH (20 ml) and hydrogenated over 10% Pd—C catalyst under atmospheric pressure, during 1 h at room temperature. Next, the catalyst was filtered off and washed with MeOH The combined filtrates were evaporated to dryness under reduced pressure to oil. Yield: 0,072 g (100%) of N-(amidino)-4-(D-leucyl-L-leucylamino)butylamine.

To a solution of DIPEA (70 µl, 0.40 mmol), HOBt (0.027 g, 0.20 mmol), 7-hydroxy-4-coumarinacetic acid (or (7-hydroxycoumarin-4-yl) acetic acid) (0.045 g, 0.20 mmol) in DMF (4 ml) and N-(amidino)-4-(D-leucyl-L-leucylamino)butylamine (0.072 g, 0.20 mmol), TBTU (0.065 g, 0.20 mmol) was added. After stirring during 12 h at room temperature, the solution was evaporated to dryness. The residue was dissolved in mixture of solvents (1 ml DMF, 0.5 ml MeOH, 1.5 ml H$_2$O) and purified by semipreparative reversed-phase HPLC on Kromasil column (25×250 mm, C-8, 5 µm), by isocratic elution with 15% acetonitrile/water solution containing 0.1% TFA, at flow rate 14 ml/min. The eluate was monitored using UV detector at λ=226 nm. Fractions containing desired product were concentrated under reduced pressure and lyophilized.

Yield: 11 mg (10%) of N-(amidino)-4-(7-hydroxy-4-coumarinacetyl-D-leucyl-L-leucylamino)butylamine as trifluoracetate salt. The purity was confirmed by analytical HPLC ($R_t$=13.78 min in 30% acetonitrile/water solution containing 0.1% TFA) and MS IT-TOF analysis (m/z 559.8 [M+H]$^+$; calculated for $C_{28}H_{42}N_6O_6$: 558.7).

Example 2

Synthesis of Coumarinacetyl Derivative A-107

(2S)-1-(N-benzyloxycarbonyl-L-phenylalanylamino-2-(tert-butoxycarbonylamino)-3-methylbutane The (2S)-1-amino-2-tert-butyloxycarbonylamino-3-methylbutane hydrochloride was obtained from tert-butyloxycarbonyl-L-valinol in accordance with the literature procedures (Mattingly, P. G., Synthesis, 1990, 1990, 366-368. Desired Boc-protected alcohol was obtained from Boc-L-valine, in accordance with the literature procedure (Juszczyk, P. et al., Letters In Peptide Science. 2003, 10, 79-82). The solution of (2S)-1-amino-2-tert-butyloxycarbonylamino-3-methylbutane hydrochloride (0.50 g, 2.096 mmol), Z-L-phenylalanine (0.659 g, 2.20 mmol), triethylamine (611 µl, 4.4 mmol) and HOBt (0.297 g. 2.20 mmol) in 10 ml of DMF was cooled on ice bath and DCC (0.498 g, 2.42 mmol) was added in small portions, during 0.5 h. The stirring was continued during 1 hour, next the reaction mixture was left in room temperature overnight. The precipitated DCU was filtered off, washed with DMF (2×3 ml) and the combined filtrates were evaporated under reduced pressure. The solid residue was dissolved in ethyl acetate (200 ml) and the solution was washed with 1 M hydrochloric acid (3×70 ml),
water (70 ml), 1 M sodium bicarbonate (3×70 ml) and brine (3×70 ml). The organic layer was dried over anhydrous magnesium sulphate and evaporated under reduced pressure. The residue was dissolved in ethyl acetate and precipitated with petroleum ether.

Yield: 0.743 g (85%) of (2S)-1-(N-benzyloxycarbonyl-L-phenylalanylamino)-2-(tert-butoxycarbonylamino)-3-methylbutane.

$[\alpha]^{20}_D$=−12.7° (c=1, methanol). MALDI-TOF analysis: m/z 506.2 [M+Na]$^+$, 522.2 [M+K]$^+$ calculated for $C_{27}H_{37}N_3O_5$: 483.6.

(2S)-1-(N-benzyloxycarbonyl-L-phenylalanylamino)-2-(N-tert-butoxycarbonyl-L-leucylamino)-3-methylbutane (2S)-1-(N-benzyloxycarbonyl-L-phenylalanylamino)-2-(tert-butoxycarbonylamino)-3-methylbutane (0.730 g, 1.51 mmol) was dissolved in 15 ml of 4N solution of anhydrous hydrochloride in dioxane. The reaction mixture was stirred during 0.5 h at room temperature, then evaporated under reduced pressure. The residual oil was triturated with anhydrous diethyl ether (50 ml). The obtained solid was filtered off under reduced pressure, washed with anhydrous diethyl ether (3×10 ml) and dried under vacuum over potassium hydroxide. The resulted (2S)-2-amino-1-(N-benzyloxycarbonyl-L-phenylalanylamino)-2-(tert-butoxycarbonyl-amino)-3-methylbutane hydrochloride (0.622 g, 1.48 mmol) was dissolved in 14 ml DMF/DCM (5:9 v/v) mixture, then triethylamine (412 µl, 2.96 mmol), HOBt (0.200 g, 1.48 mmol) and Boc-L-leucine (0.342 g, 1.48 mmol) were added to the solution. The mixture was cooled on ice bath and DCC (0.336 g, 1.63 mmol) was added in small portions during 0.5 h, with vigorous stirring. Stirring on ice bath was continued during additional 1 h, then the reaction mixture was left at room temperature overnight. The precipitated DCU was filtered off, washed with DMF (5 ml) and the combined filtrates were evaporated under reduced pressure. The solid residue was dissolved in 250 ml of ethyl acetate and the solution was washed with 1 M hydrochloric acid (3×80 ml), water (100 ml), 1 M sodium bicarbonate (3×80 ml) and saline (3×80 ml). The organic layer was dried over anhydrous magnesium sulphate and evaporated to dryness. The residue was dissolved in hot toluene and precipitated with petroleum ether, yielding 0.795 g (90%) of (2S)-1-(N-benzyloxycarbonyl-L-phenylalanylamino)-2-(N-tert-butoxycarbonyl-L-leucylamino)-3-methylbutane.

$[\alpha]^{20}_D$=−21.6° (c=1, methanol). MALDI-TOF analysis: m/z 619.2[M+Na]$^+$, 635.2 [M+K]$^+$ calculated for $C_{33}H_{48}N_4O_6$: 596.8.

(2S)-1-(N-benzyloxycarbonyl-L-phenylalanylamino)-2-[N-tert-butoxycarbonyl-5-aminopentanoyl-L-leucylamino]-3-methylbutane (2S)-1-(N-benzyloxycarbonyl-L-phenylalanylamino)-2-[(N-tert-butoxycarbonyl)-5-aminopentanoyl-L-leucylamino]-3-methylbutane (0.785 g, 1.13 mmol) was dissolved in 15 ml of 4N solution of anhydrous hydrochloride in dioxane. The reaction mixture was stirred during 0.5 h at room temperature, then evaporated to dryness under reduced pressure. The residual oil was triturated with anhydrous diethyl ether (50 ml). Obtained solid was filtered off under reduced pressure, washed with anhydrous diethyl ether (3×10 ml) and dried under vacuum, over potassium hydroxide. The resulted (2S)-1-(N-benzyloxycarbonyl-L-phenylalanylamino)-2-(L-leucylamino)-3-methylbutane hydrochloride (0.687 g, 1.29 mmol) was dissolved in 10 ml DMF/DCM (v/v 5:9) and triethylamine (359 µl, 2.58 mmol), HOBt (0.174 g, 1.29 mmol), N-tert-butoxycarbonyl-5-aminopentanoic acid (0.275 g, 1.29 mmol) were added to the solution. The mixture was cooled in an ice bath, then DCC (0.292 g, 1.42 mmol) was added in small portions, during 0.5 h with vigorous stirring. The mixture was stirred in an ice bath for additional 1 h, then left at room temperature overnight. The precipitated DCU was filtered off, washed with DMF (5 ml) and the combined filtrates were evaporated under reduced pressure. The solid residue was dissolved in 250 ml of ethyl acetate and the solution was washed with 1 M hydrochloric acid (3×80 ml), water (100 ml), 1 M sodium bicarbonate (3×80 ml) and saline (3×80 ml). The organic layer was dried over anhydrous magnesium sulphate and evaporated to dryness. The residue was dissolved in hot toluene and precipitated with petroleum ether, yielding 0.817 g (96%) of (2S)-1-(N-benzyloxycarbonyl-L-phenylalanylamino)-2-[N-tert-butoxycarbonyl-5-aminopentanoyl-L-leucylamino]-3-methylbutane.

$[\alpha]_D^{20}$ =−17.2° (c=1, methanol). MALDI-TOF analysis: m/z 718.0 [M+Na]$^+$, 733.9 [M+K]$^+$; calculated for $C_{38}H_{57}N_5O_7$: 695.9.

(2S)-2-[N-tert-butoxycarbonyl-5-aminopentanoyl-L-leucylamino]-1-[N-(7-hydroxy-4-coumarinacetyl)-L-phenylalanylamino]-3-methylbutane (2S)-1-(N-butoxycarbonyl-L-phenylalanylamino)-2-[N-tert-butoxycarbonyl-5-aminopentanoyl-L-leucylamino]-3-methylbutane (0.800 g. 1.15 mmol) was dissolved in methanol (25 ml) and hydrogenated over 10% Pd—C catalyst under atmospheric pressure during 1 h, at room temperature. Next, the catalyst was filtered off and washed with MeOH and the combined filtrates were evaporated to dryness under reduced pressure to oil. Yield: 0.646 g (100%).

To cooled on ice bath and vigorously stirred solution of (2S)-2-[N-tert-butoxycarbonyl-5-aminopentanoyl-L-leucylamino]-1-(L-phenylalanylamino)-3-methylbutane (0.646 g. 1.15 mmol), 7-hydroxy-4-coumarinacetic acid (0.253 g, 1.15 mmol), HOBt (0.155 g, 1.15 mmol), DIPEA (394 µl, 2.30 mmol) in DMF (10 ml), DCC (0.261 g, 1.27 mmol) was added in small portions, during 0.5 h. The mixture was stirred on ice bath for additional 1 h, next left at room temperature overnight. The precipitated DCU filtered off, washed with DMF (5 ml) and the combined filtrates were evaporated under reduced pressure. Obtained solid residue was dissolved in ethyl acetate (250 ml) and the solution was washed with 1 M hydrochloric acid (3×80 ml), water (100 ml), 1 M sodium bicarbonate (3×80 ml) and brine (3×80 ml). The organic layer was dried over anhydrous magnesium sulphate and evaporated to dryness. The residue was dissolved in hot toluene and precipitated with petroleum ether, Yield: 0.799 g (91%) of (2S)-2-[N-tert-butoxycarbonyl-5-aminopentanoyl-L-leucylamino]-1-[N-(7-hydroxy-4-coumarinacetyl)-L-phenylalanylamino]-3-methylbutane;

$[\alpha]_D^{20} = -16.0°$ (c=1, methanol). MS IT-TOF analysis: m/z 764.4 $[M+H]^+$; calculated for $C_{41}H_{57}N_5O_9$: 763.4.

(2S)-2-[N-(5-guanidinepentanoyl)-L-leucylamino]-1-[N-(7-hydroxy-4-coumarinylacetyl-L-phenylalanylamino)-3-methylbutane (2S)-2-[N-tert-butoxycarbonyl-5-aminopentanoyl-L-leucylamino]-1-[N-(7-hydroxy-4-coumarinacetyl-L-phenylalanylamino)-3-methylbutane (0.100 g, 0.131 mmol) was dissolved in 10 ml of 4N solution of anhydrous hydrochloride in dioxane. The reaction mixture was stirred during 0.5 h at room temperature and then evaporated to dryness under reduced pressure. The residual oil was triturated with anhydrous diethyl ether (30 ml). The obtained solid was filtered off under reduced pressure, washed with anhydrous diethyl ether (2×10 ml) and dried under vacuum over potassium hydroxide. The resulted (2S)-2-(N-(5-aminopentanoyl)-L-leucylamino)-1-[N-(7-hydroxy-4-coumarinylacetyl)-L-phenylalanylamino]-3-methylbutane (0.099 g, 0.142 mmol) was dissolved in 5 ml of DMF/MeOH (v/v, 1:1). Next, triethylamine (39 μl, 0.28 mmol), 3,5-dimethyl-1-pyrazolylformamidinium nitrate (0.086 g, 0.43 mmol) was added. The pH of the mixture was kept about 9.5. After five days, the solution was evaporated and the resulted residue was dissolved in 3 ml of mixture DMSO/water (2:1, v/v). The solution was injected on the RP-HPLC column (25×250 mm, Kromasil C-8, 5 μm) and eluted with 30% acetonitrile/water solution containing 0.1% TFA (isocratic elution), at flow rate 14 ml/mm. The eluate was monitored using UV detector at λ=226 nm. Fractions containing pure desired product were collected, concentrated under reduced pressure and lyophilized.

Yield: 9 mg (9%) of (2S)-2-[N-(5-guanidinepentanoyl)-L-leucylamino]-1-[N-(7-hydroxy-4-coumarinylacetyl)-L-phenylalanylamino]-3-methylbutane as trifluoroacetate salt.

The purity was confirmed by analytical HPLC($R_t$=15.11 min. in 36% acetonitrile/water/0.1% TFA solution) and MS IT-TOF analysis (m/z 706.2 $[M+H]^+$; calculated for $C_{37}H_{51}N_7O_7$: 705.4).

Example 3

Inhibition of Osteoclast Formation
Spleen Cell Cultures

Cells were obtained from spleens of 5- to 9-week-old mice. The spleens were dissected free of adhering tissues, and cells were released by rubbing the spleens against the bottom of a Petri dish, in which grooves had been made by a scalpel. Erythrocytes were lysed in red blood cell lysis buffer (0.16 MNH4Cl, 0.17 M Tris, pH7.65) and the remaining cells were seeded, at a cell density of 106 cells/cm2, on plastic coverslips placed in 24-well plates. The cells were cultured in 0.5 ml a-minimal essential medium (a-MEM) supplemented with 10% fetal bovine serum (FBS), L-glutamine (0.7 mM), 100 U/ml benzylpenicillin, 100 mg/ml streptomycin and 100 mg/ml gentamycin sulphate. Cells were allowed to settle overnight in complete medium and thereafter the medium was changed and the experiment started. Osteoclast precursor cells were induced to proliferate and differentiate by the addition of M-CSF (25 ng/ml) and RANKL (100 ng/ml). To study the effect of the compounds on osteoclastogenesis, cells were grown in medium containing compounds at different concentrations, together with M-CSF and RANKL. Cells cultured in complete medium without M-CSF and RANKL were included in all experiments as a control. Medium was changed after 3 days. After 1-6 days, the cells were washed three times with PBS (pH 7.35) and fixed with acetone in citrate buffer/3% formaldehyde solution. Cells were then stained for tartrate-resistant acid phosphatase (TRAP) activity using the SigmaDiagnostics Acid Phosphatase Leukocyte staining kit and by following the manufacturer's instruction. Multinucleated (no. of nuclei>3), TRAP-positive cells were counted as osteoclasts (TRAPC-MuOCL). Osteoclasts formed in the spleen cell cultures stimulated by M-CSF and RANKL were able to form pits when cultured on slices of devitalised bovine bone and the stimulation of osteoclastogenesis was associated with increased mRNA expression of several osteoclast genes including ctr, trap and cathepsin K. No osteoclasts were formed when cells were treated with either M-CSF or RANKL alone and the stimulation caused by M-CSF and RANKL was abolished by osteoprotegerin (OPG). No osteoclasts were formed in the presence of PTH or 1,25(OH)2-vitamin D3 (D3) indicating the lack of stromal cells in the spleen cell cultures.

Bone Marrow Macrophage Cultures

Highly purified BMMs were isolated according to Takeshita et al. (2000). These cells did not express alkaline phosphatase, RANKL, OPG or CTR mRNA, but mRNA for RANK, c-Fms, cathepsin K and TRAP, as assessed by quantitative real-time PCR (data not shown).

For osteoclastogenesis experiments, BMMs were seeded either on 0.8 $cm^2$ glass chamber slides or 0.32 $cm^2$ 96-well plates at a density of $10^4$ cells/$cm^2$ in a-MEM/10% FBS containing either 100 ng/ml M-CSF (controls) or 100 ng/ml M-CSF C50 ng/ml RANKL, with and without test compounds. After 4-5 days, with a change of medium after 3 days, the cultures were harvested and the cells fixed with acetone in citrate buffer/3% formaldehyde and subsequently stained for TRAP. The TRAP-positive cells with three or more nuclei were considered osteoclasts, and the number of multinucleated osteoclasts was counted ($TRAP^+$-MuOCL). Osteoclasts formed in these cultures stimulated by M-CSF and RANKL were able to form pits when cultured on slices of bovine bone and osteoclast formation was associated with increased mRNA expression of CTR, TRAP and cathepsin K. Osteoclasts were not formed in the presence of PTH or D3, indicating the lack of stromal cells in the cultures. Osteoclast formation caused by M-CSF and RANKL was abolished by OPG

TABLE 1

BMM #27 + BMM #29 + BMM #30 + BMM #34. Four different experiments with purified bone marrow macrophages stimulated with M-SCF and RANKL to induce formation of trap+ multinucleated osteoclasts with and without different compounds.

| Comp. | Papain Ki nM | Cath K Ki nM | Cath B Ki nM | Osteoclast formation (100% = M-CSF + RANKL) |
|---|---|---|---|---|
| A-25 | Inactive | 42.2 | 8.1 | 1% |
| A-11 | 93 | 14 | 360 | 1% |
| A-12 | 94 | 13 | 1000 | 2% |
| A-33 | 46 | 24 | 2 | 0% |
| A-16 | 340 | inactive | inactive | 16% |
| A-47 | 16 | 99 | 0.3 | 0% |
| A-42 | 161 | inactive | 14 | 0% |
| A-50 | 68 | 63 | 55 | 2% |

TABLE 1-continued

BMM #27 + BMM #29 + BMM #30 + BMM #34. Four different experiments with purified bone marrow macrophages stimulated with M-SCF and RANKL to induce formation of trap+ multinucleated osteoclasts with and without different compounds.

| Comp. | Papain Ki nM | Cath K Ki nM | Cath B Ki nM | Osteoclast formation (100% = M-CSF + RANKL) |
|---|---|---|---|---|
| A-54 | 1000 | 14 | 228 | 1% |
| Z-RLR | 9 | 1 | 0.0005 | 0% |
| A-20 | Inactive | Nd | Nd | 0% |
| M-1 | 23 | 160 | 3 | 14% |
| A-40 | Nd | Nd | Nd | 0% |
| A-49 | Nd | Nd | Nd | 0.2% |
| A-55 | Nd | Nd | Nd | 0.2% |
| A-59 | Nd | Nd | Nd | 0% |

TABLE 2

BMM #141 and BMM #142. experiments with purified bone marrow macrophages stimulated with M-SCF and RANKL to induce formation of trap+ multinucleated osteoclasts with and without different compounds

| Comp. | Osteoclast formation (100% = M-CSF + RANKL) |
|---|---|
| A-107 | 0% |
| A-127 | 16% |
| A-128 | 4% |
| A-52 | 15% |
| A-55 | 8% |
| Cystatin C | 0% |

The invention claimed is:

1. A method of treating a condition associated with bone loss or low bone density or for inhibiting osteoclast differentiation and stimulation or bone resorption in a mammal in need thereof, comprising administering to said mammal an effective amount of one or more compounds selected from the group consisting of A-20, A-33, A-42, A-47, A-59, and A-107:

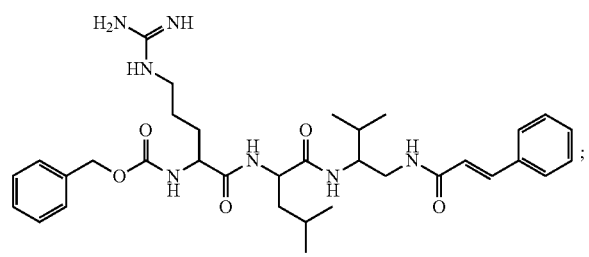

Sequence: Z-Arg-Leu-NH—CH(iPr)·CH$_2$·NH ← Cin

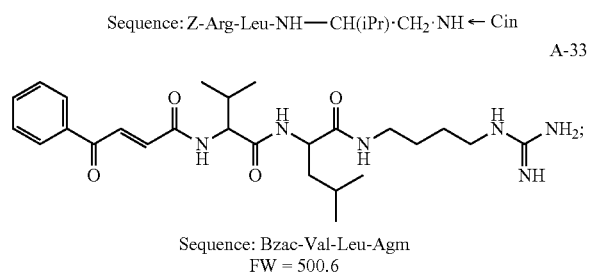

Sequence: Bzac-Val-Leu-Agm
FW = 500.6

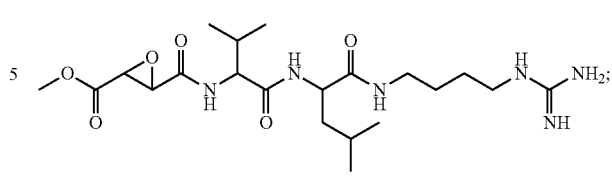

Sequence: MeO-Eps-Val-Leu-Agm
FW = 470.6

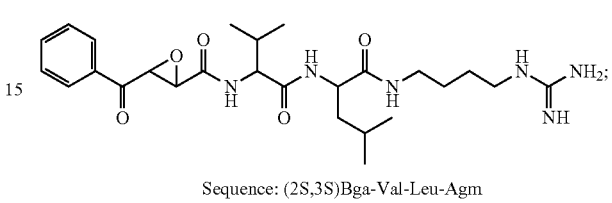

Sequence: (2S,3S)Bga-Val-Leu-Agm
FW = 516.6

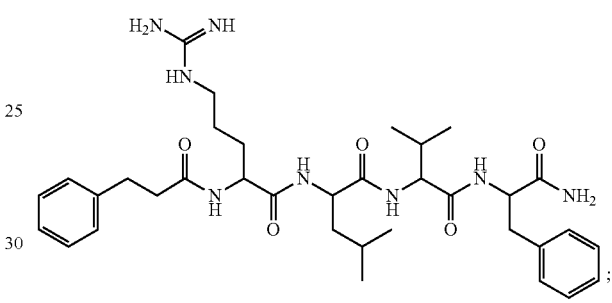

Sequence:
Ppa-Arg-Leu-Val-Phe-NH$_2$ or dPhe-Arg-Leu-Val-Phe-NH$_2$,
where Ppa = dPhe = deamino-Phe = 3-phenylpropionic acid

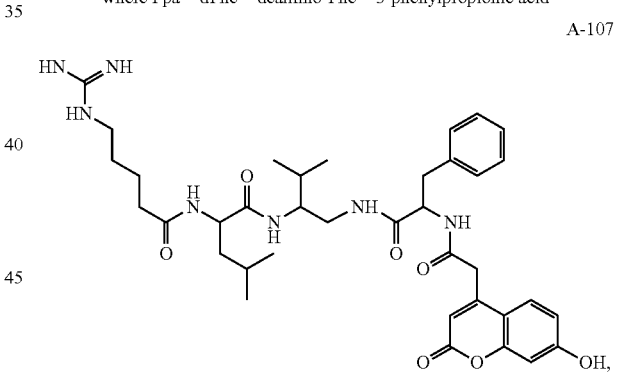

the one or more compound being a single stereoisomer or a mixture of different stereoisomers, or a pharmaceutically acceptable salt thereof.

2. The method according to claim 1, wherein the compound is administered as a pharmaceutical composition comprising a pharmaceutically acceptable carrier, buffer, excipient or diluent.

3. The method according to claim 1, wherein the one or more compound is administered in a prosthetic device.

4. The method according to claim 1, wherein the condition is a bone disease selected from the group consisting of osteoporosis, juvenile osteoporosis, osteogenesis imperfecta, hypercalcaemia, hyperparathyroidism, osteomalacia, osteohalisteresis, osteolytic bone disease, osteonecrosis and Paget's disease of bone, or the condition is a secondary osteoporosis of bone loss due to rheumatoid arthritis, inflammatory arthritis, osteomyelitis, bone loss due to an eating disorder, metastatic bone diseases, periodontal bone loss, bone loss due to cancer, age-related loss of bone, or bone resorption induced by pharmaceuticals or implants.

5. A method of treating a subject suffering from a high level of bone resorption, comprising administering to the subject an effective amount of one or more compounds selected from the group consisting of A-20, A-33, A-42, A-47, A-59, and A-107, as defined in claim 1.

6. A method of inhibiting osteoclast formation or activity in a subject in need thereof, comprising administering to the subject an effective amount of one or more compounds selected from the group consisting of A-20, A-33, A-42, A-47, A-59, and A-107, as defined in claim 1.

7. The method according to claim 6, wherein the subject is suffering from osteoporosis.

8. The method according to claim 1, wherein the one or more compounds are selected from the group consisting of A-33, A-42, A-47, A-59, and A-107.

9. The method according to claim 1, wherein the method is for treating a condition associated with bone loss or low bone density, and the one or more compounds are selected from the group consisting of A-33, A-42, A-47, A-59, and A-107.

\* \* \* \* \*